United States Patent
Alomair et al.

(10) Patent No.: US 11,971,338 B2
(45) Date of Patent: Apr. 30, 2024

(54) MULTI-HEAT ENERGY SOURCE CORE SAMPLE HOLDER ASSEMBLY

(71) Applicant: Kuwait University, Safat (KW)

(72) Inventors: Osamah A. S. Alomair, Safat (KW); Nyeso Christian Azubuike, Safat (KW); Ahmad Essam Abdel Halim Omar, Safat (KW)

(73) Assignee: Kuwait University, Safat (KW)

(*) Notice: Subject to any disclaimer, the term of this patent is extended or adjusted under 35 U.S.C. 154(b) by 293 days.

(21) Appl. No.: 17/672,852

(22) Filed: Feb. 16, 2022

(65) Prior Publication Data
US 2023/0258546 A1    Aug. 17, 2023

(51) Int. Cl.
| | | |
|---|---|---|
| G01N 1/44 | (2006.01) | |
| E21B 25/00 | (2006.01) | |
| G01N 33/24 | (2006.01) | |
| H05B 1/02 | (2006.01) | |
| H05B 11/00 | (2006.01) | |

(52) U.S. Cl.
CPC ............. *G01N 1/44* (2013.01); *E21B 25/005* (2013.01); *G01N 33/24* (2013.01); *H05B 1/0227* (2013.01); *H05B 11/00* (2013.01); *H05B 2213/00* (2013.01)

(58) Field of Classification Search
CPC ........ E21B 25/005; G01N 33/24; G01N 1/44; H05B 1/0228; H05B 11/00; H05B 2213/00
See application file for complete search history.

(56) References Cited

U.S. PATENT DOCUMENTS

| | | | | |
|---|---|---|---|---|
| 2,864,929 A | * | 12/1958 | Schwing | H05B 3/06 219/536 |
| 2010/0126266 A1 | * | 5/2010 | Coenen | G01N 33/241 250/255 |
| 2011/0050223 A1 | * | 3/2011 | Balcom | G01R 33/305 324/318 |
| 2014/0340082 A1 | * | 11/2014 | Yang | G01N 24/081 324/309 |
| 2023/0095025 A1 | * | 3/2023 | Kuznetcov | G01N 27/026 324/649 |

* cited by examiner

*Primary Examiner* — Kristina M Deherrera
*Assistant Examiner* — Jean F Morello
(74) *Attorney, Agent, or Firm* — Schott, P.C.

(57) ABSTRACT

A multi-heat energy source core sample holder assembly for conducting experiment on a core sample includes a core sample holder, a flexible sleeve, and a multi-heat energy generation source arrangement. The core sample holder includes a cylindrical pressure chamber and a pair of disk-shaped flanges positioned along opposite ends of the cylindrical pressure chamber to accommodate at least one fluid injection port and at least one fluid discharge port. The flexible sleeve is arranged within and along the cylindrical pressure chamber to define one or more section(s) to hold the core sample. The energy generation source includes a wire member to be coiled along an internal wall of the flexible sleeve to be supplied with electric current in at least one of a Direct Current (DC) form to produce an electric resistance heating, or an Alternate Current (AC) form to produce an electromagnetic heating, singularly or in combination.

18 Claims, 2 Drawing Sheets

MULTI-HEAT ENERGY SOURCE CORE SAMPLE HOLDER ASSEMBLY

FIELD OF THE DISCLOSURE

The present disclosure relates to oil and gas industry, and, more particularly, relates to a multi-heat energy source core sample holder assembly for conducting experimentation on core samples containing hydrocarbon or geologic rock properties in a laboratory.

BACKGROUND OF THE DISCLOSURE

In the oil and gas production industry it is common practice to take, when wells are being drilled, one or more cylindrical core samples containing hydrocarbon or geologic rock properties to subsequently perform one or more tests with such core sample in a laboratory. Most of such core samples are collected during the exploration, production or appraisal well drilling operation phase in the field development. Such well drilling is aimed at identifying the "sweet spots" appropriate for further exploration or for the positioning of actual production well to extract the formation fluid, and to obtain a range of useful parameters regarding the underground formation rock and fluid, the collected core samples are subjected to petrophysical investigation using different standards and methods.

However, as the well depth used by the oil and gas industry continuous to increase, correspondingly, the pressure and temperature downhole continuous to rise. Therefore, efforts to reproduce this down-hole conditions in the laboratory may require instrumentation that can withstand these high pressure and temperature condition of a typical hydrocarbon reservoir. This way, the correlation between the data extracted from the downhole and those determined from a controlled laboratory condition is improved, and the prediction accuracy of the targeted "sweet spots" or actual producing reservoir is increased.

A key instrument that provides this synthetic downhole pressure and temperature condition, as well as the possibility of confining the representative core sample and fluid to a typical reservoir condition is a specially designed core holder, wherein the core samples are placed, and reservoir fluids are injected on one side and discharged on the opposite side while the migration and fluid-rock interactions are studied. The typical reservoir condition overburden or confining pressure is obtained in the laboratory by introducing a high-pressure secondary fluid source outside the rock at the equivalent down-hole temperature.

Although different types of core sample holder have been developed and used during rock analysis in attempt to mimic the reservoir condition while studying the migration of fluid in porous media and simultaneously determining relevant properties, a prevailing setback of the existing core sample holder is the extended time required for heating the core sample in the sample holder to a desired reservoir temperature condition, because the heat is supplied from an external jacket, or the entire holder is placed inside a heating oven. This way, the supplied heat may first penetrate the thick tubular hull and the poor heat conducting rubber sleeve before reaching the core sample which is the heat target. This method of heating is proven to be time consuming and inefficient in most cases, particularly, when a certain high reservoir temperature condition is required.

Accordingly, there exists a need to overcome shortcomings of the conventional devices and methods. Consequently, a thoughtful need has been recognized for the development of a reservoir core sample holder which provides a faster and efficient heating to the core sample and fluid in the core holder to any temperature condition.

SUMMARY OF THE DISCLOSURE

In view of the foregoing disadvantages inherent in the prior art, the general purpose of the present disclosure is to provide a multi-heat energy source core sample holder assembly for conducting experimentation on core samples containing hydrocarbon or geologic rock properties in a laboratory, to include all advantages of the prior art, and to overcome the drawbacks inherent in the prior art.

An object of the present disclosure is to provide multi-heat energy source core sample holder assembly for conducting laboratory scale investigation on core samples containing hydrocarbon or geologic rock properties.

The further object of the present invention is to provide an improvement to existing core holder designs by incorporating multiple heat energy sources into a single core holder assembly, including electrical and electromagnetic heat energy.

In light of the above objects, in one aspect of the present disclosure, a multi-heat energy source core sample holder assembly for conducting experimentation on core samples containing hydrocarbon or geologic rock properties in a laboratory is provided. The multi-heat energy source core sample holder includes a core sample holder, a flexible sleeve, and a multi-heat energy generation source arrangement. The core sample holder may include a cylindrical pressure chamber and a pair of disk-shaped flanges positioned along opposite ends of the cylindrical pressure chamber. The pair of disk-shaped flanges defines a first disk-shaped flange and a second disk-shaped flange. The first disk-shaped flange accommodates at least one fluid injection port, and the second disk-shaped flange accommodates at least one fluid discharge port. Further, the flexible sleeve is arranged within and along the cylindrical pressure chamber to define one or more section(s) to hold the core sample, and the flexible sleeve is adapted to be securely sealed within the cylindrical pressure chamber to the pair of disk-shaped flanges and the core sample.

Furthermore, the multi-heat energy generation source arrangement includes a wire member, at least one energy inlet port, at least one circuit breaker member, and at least one elongated thermocouple member. The wire member is coiled along an internal wall of the flexible sleeve. The at least one energy inlet port is electrically coupled with the wire member to supply electric current along the wire member in at least one of a Direct Current (DC) form to produce an electric resistance heating, or an Alternate Current (AC) form to produce an electromagnetic heating, singularly or in combination. The at least one circuit breaker member is electrically coupled to the wire member and the at least one energy inlet port to control the supply of electric current across the one or more section(s) within the flexible sleeve depending upon a length of the core sample for a given experiment. The at least one elongated thermocouple member is electrically configured to monitor a temperature inside one or more section(s) of the flexible sleeve.

In one embodiment, the multi-heat energy source core sample holder assembly may further include an elastomeric O-ring. Each of the first and second disk-shaped flange comprises a circumferential groove along which the elastomeric O-ring is disposed to form a high-pressure seal between each of the first and second disk-shaped flange and an inner surface along respective opposite ends of the cylindrical pressure chamber.

In one embodiment, the multi-heat energy source core sample holder assembly may further include an annular space defined between the cylindrical pressure chamber and the flexible sleeve. In one further embodiment, the multi-heat energy source core sample holder assembly may further include at least one fluid injection port pierced through the cylindrical pressure chamber to extend up to the annular space to inject a confining fluid in the annular space. In an example the confining fluid is one of water, oil or gas.

In one embodiment, the multi-heat energy source core sample holder assembly may further include a pressure control member arranged in the annular space to maintain the confining fluid in the annular space at a predetermined pressure.

In one example, the core sample holder may include a threaded profile formed along an inner surface along each of the opposite ends to threadedly coupled with the pair of disk-shaped flanges positioned along opposite ends of the cylindrical pressure chamber.

In one embodiment, each of the first disk-shaped flange and the second disk-shaped flange of the pair of disk-shaped flanges comprises an end plug on which respective opening of the at least one fluid injection port to inject reservoir fluids, and at least one fluid discharge port to discharge the reservoir fluids while the migration and core sample interactions are studied.

In one embodiment, the multi-heat energy source core sample holder assembly may further include a sand-screen assembly coupled to respective end plugs of the first disk-shaped flange and the second disk-shaped flange of the pair of disk-shaped flanges to restrict the migration of fine particles from the core sample.

In one embodiment, the cylindrical pressure chamber may be composed of one of carbon fiber composite material or its equivalent steel grade material, and the flexible sleeve may be composed of a flexible neoprene rubber with an internal Teflon (polytetrafluoroethylene PTFE) lining. In one embodiment, the wire member is a nichrome metal wire.

In one embodiment, the at least one energy inlet port, the at least one circuit breaker member, and the at least one elongated thermocouple member are pierced through the cylindrical pressure chamber into the flexible sleeve to be electrically coupled with the wire member.

In one another aspect, the present disclosure provides a multi-heat energy generation source arrangement for a multi-heat energy source core sample holder assembly to conduct experiment on a core sample. The multi-heat energy generation source arrangement includes a wire member, at least one energy inlet port and at least one circuit breaker member. The wire member is coiled along an internal wall of a flexible sleeve accommodated with a cylindrical pressure chamber of a core sample holder. The at least one energy inlet port is electrically coupled with the wire member to supply electric current along the wire member in at least one of a Direct Current (DC) form to produce an electric resistance heating, or an Alternate Current (AC) form to produce an electromagnetic heating, singularly or in combination. The at least one circuit breaker member is electrically coupled to the wire member and the at least one energy inlet port to control the supply of electric current across the one or more section(s) within the flexible sleeve depending upon a length of the core sample for a given experiment.

In one embodiment, the multi-heat energy generation source arrangement further includes at least one elongated thermocouple member to monitor a temperature inside one or more section(s) of the flexible sleeve.

In one embodiment, the at least one energy inlet port, the at least one circuit breaker member, and the at least one elongated thermocouple member are pierced through the cylindrical pressure chamber into the flexible sleeve to be electrically coupled with the wire member, and that the wire member is a nichrome metal wire.

This together with the other aspects of the present disclosure, along with the various features of novelty that characterize the present disclosure, is pointed out with particularity in the claims annexed hereto and forms a part of the present disclosure. For a better understanding of the present disclosure, its operating advantages, and the specified object attained by its uses, reference should be made to the accompanying drawings and descriptive matter in which there are illustrated exemplary embodiments of the present disclosure.

BRIEF DESCRIPTION OF THE DRAWINGS

The advantages and features of the present disclosure will become better understood with reference to the following detailed description taken in conjunction with the accompanying drawing, in which.

Like reference numerals refer to like parts throughout the description of several views of the drawing.

DETAILED DESCRIPTION OF THE DISCLOSURE

The exemplary embodiments described herein detail for illustrative purposes are subject to many variations in implementation. The present disclosure provides a multi-heat energy source core sample holder assembly for conducting laboratory scale investigation on core samples containing hydrocarbon or geologic rock properties. It should be emphasized, however, that the present disclosure is not limited only to what is disclosed and extends to cover various alternation to a multi-heat energy source core sample holder assembly. It is understood that various omissions and substitutions of equivalents are contemplated as circumstances may suggest or render expedient, but these are intended to cover the application or implementation without departing from the spirit or scope of the present disclosure.

The terms "a" and "an" herein do not denote a limitation of quantity, but rather denote the presence of at least one of the referenced items.

The terms "having", "comprising", "including", and variations thereof signify the presence of a component.

Figure 1:
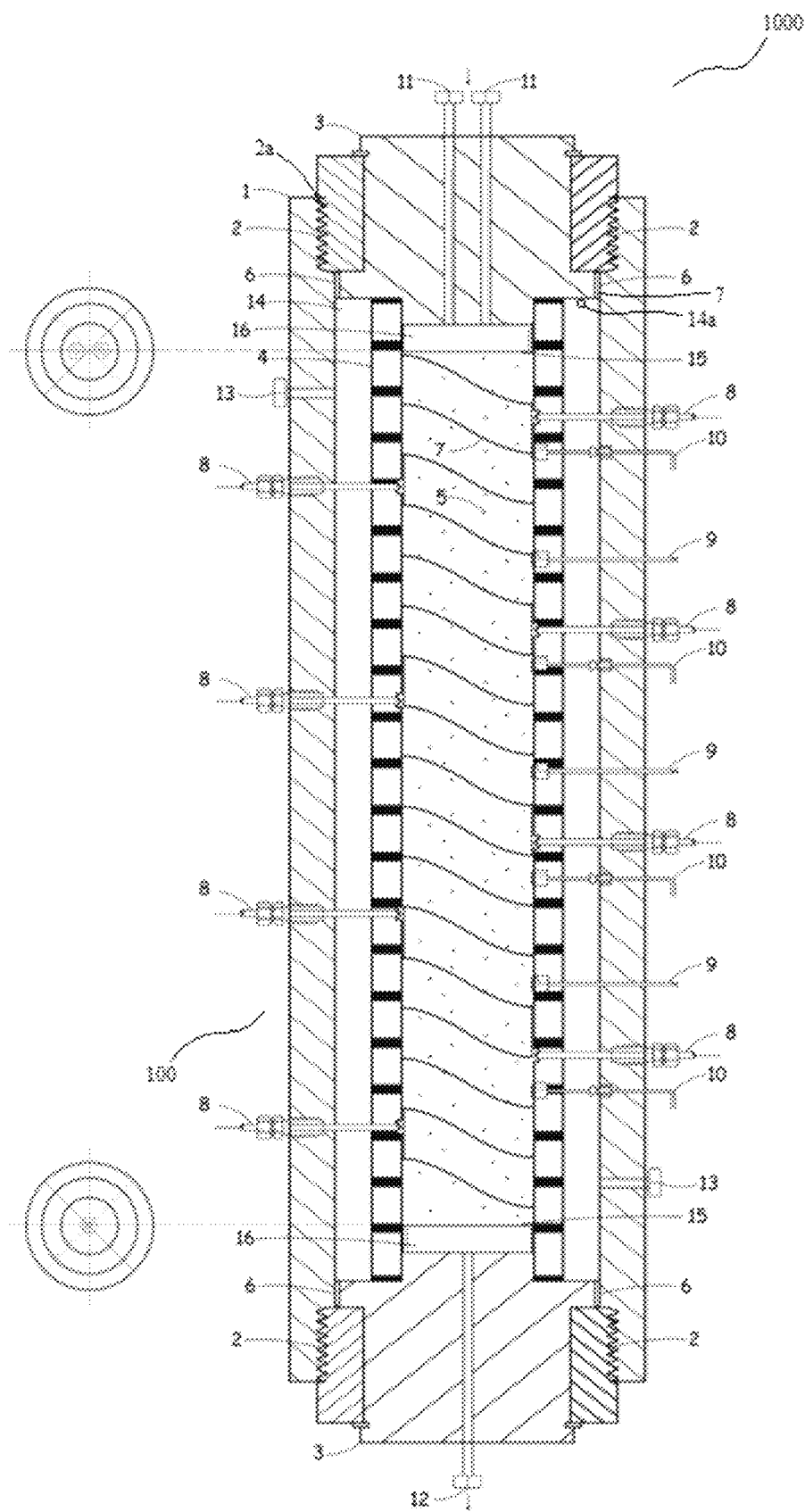
FIG. 1 illustrates a schematic of the present invention core holder assembly, in accordance with an exemplary embodiment of the present disclosure.
Figure 2:
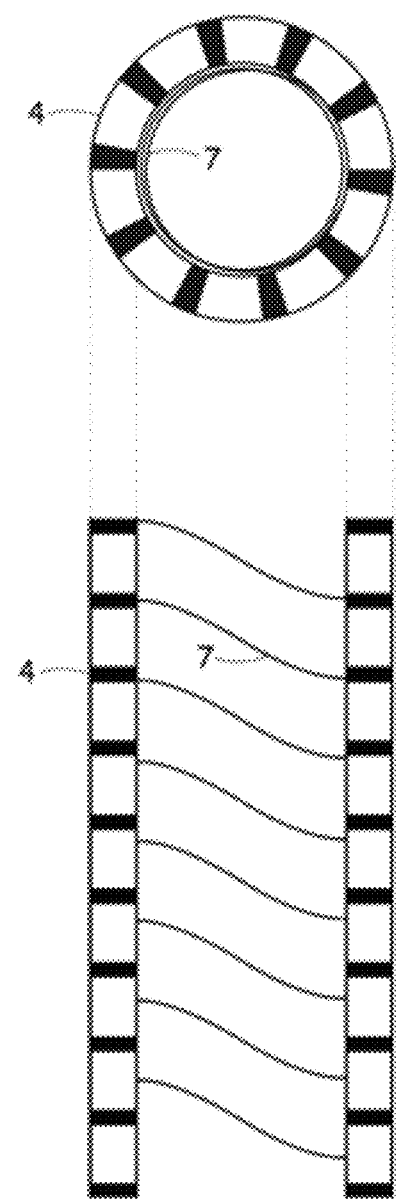
FIG. 2 illustrates a cross-sectional view of the rubber sleeve with internal nichrome wire coiling, in accordance with an exemplary embodiment of the present disclosure.

Referring now to FIGS. 1 and 2, a multi-heat energy source core sample holder assembly 1000 will now be described, in accordance with an exemplary embodiment of the present disclosure. Specifically, FIG. 1 illustrates a schematic of the present invention core holder assembly, and FIG. 2 illustrates a cross-sectional view of the rubber sleeve with internal nichrome wire coiling, in accordance with an exemplary embodiment of the present disclosure. As seen in FIGS. 1 and 2, example views of a multi-heat energy source core sample holder assembly 1000 is illustrated to include various components that are essential to explain the present invention, and such multi-heat energy source core sample holder assembly 1000 may not be limited only those components and extends to include various other components or its arrangement that may deemed fit for this invention.

As seen in FIG. 1, a multi-heat energy source core sample holder assembly 1000 is adapted for conducting experiment on a core sample. Specifically, the multi-heat energy source core sample holder assembly 1000 is configured for laboratory scale reservoir rock flooding experiment using a representative core sample extracted from a hydrocarbon bearing formation or synthetic core samples. The core sample extends to define and include any sample from a hydrocarbon bearing formation or synthetic core samples.

As seen in FIG. 1, the multi-heat energy source core sample holder 1000 includes a core sample holder 100, a flexible sleeve 4, and a multi-heat energy generation source arrangement configured together.

The core sample holder 100 may include a cylindrical pressure chamber 1 defining opposite ends 2. In one embodiment, without departing from the scope of the present disclosure, the cylindrical pressure chamber 1 is composed of one of carbon fiber composite material or its equivalent steel grade material. The cylindrical pressure chamber 1 may be made of a steel sheet that is obtained from the Hastelloy-C steel grade which are designed to have excellent corrosion resistance in a wide range of severe environments.

The core sample holder 100 may include a pair of disk-shaped flanges 3 positioned along the opposite ends 2 of the cylindrical pressure chamber 1. In one embodiment, the core sample holder 100 may include a threaded profile 2a formed along an inner surface along each of the opposite ends 2 to threadedly coupled with the pair of disk-shaped flanges 3 positioned along opposite ends 2 of the cylindrical pressure chamber 1.

The pair of disk-shaped flanges 3 defines a first disk-shaped flange and a second disk-shaped flange. In one embodiment, the multi-heat energy source core sample holder assembly 1000 may further include an elastomeric O-ring 6. Each of the first and second disk-shaped flange comprises a circumferential groove 7 along which the elastomeric O-ring 6 is disposed to form a high-pressure seal between each of the first and second disk-shaped flange and an inner surface along respective opposite ends 2 of the cylindrical pressure chamber 1.

In one embodiment of the present disclosure, the first disk-shaped flange accommodates at least one fluid injection port 11, and the second disk-shaped flange accommodates at least one fluid discharge port 12.

In one embodiment, each of the first disk-shaped flange and the second disk-shaped flange of the pair of disk-shaped flanges 3 comprises an end plug 16 on which respective opening (not seen) of the at least one fluid injection port 11 to inject reservoir fluids into the core sample 5, and at least one fluid discharge port 12 to discharge the reservoir fluids while the its migration and core sample 5 interactions are studied.

In one embodiment, the multi-heat energy source core sample holder assembly 1000 may further include a sand-screen assembly 15 coupled to respective end plugs 16 of the first disk-shaped flange and the second disk-shaped flange of the pair of disk-shaped flanges 3 to restrict the migration of fine particles from the core sample 5.

Further, as seen in FIG. 1 and FIG. 2, the flexible sleeve 4 is arranged within and along the cylindrical pressure chamber 1 to define one or more section(s) to hold the core sample 5, and the flexible sleeve 4 is adapted to be securely sealed within the cylindrical pressure chamber 1 to the pair of disk-shaped flanges 3 and the core sample 5. In one example embodiment, without departing from the scope of the present disclosure, the flexible sleeve 4 may be composed of a flexible neoprene rubber with an internal Teflon (polytetrafluoroethylene PTFE) lining therealong.

In one embodiment, the multi-heat energy source core sample holder assembly 1000 may further include an annular space 14 defined between the cylindrical pressure chamber 1 and the flexible sleeve 4. In one further embodiment, the multi-heat energy source core sample holder assembly 1000 may further include at least one fluid injection port 13 pierced through the cylindrical pressure chamber 1 to extend up to the annular space 14 to inject a confining fluid in the annular space 14. In an example the confining fluid is one of water, oil or gas. In one embodiment, the multi-heat energy source core sample holder assembly 1000 may further include a pressure monitoring member 14a arranged in the annular space 14 to monitor and maintain the confining fluid in the annular space 14 at a predetermined pressure.

Furthermore, as seen in FIG. 1 and FIG. 2, the multi-heat energy generation source arrangement includes a wire member 7, at least one energy inlet port 8, at least one circuit breaker member 9, and at least one elongated thermocouple member 10.

The wire member 7 is coiled along an internal wall of the flexible sleeve 4. In one example embodiment, without departing from the scope of the present disclosure, the wire member 7 may be made from a good resistance material, and, such as, may include a nichrome metal wire of 0.5 mm, which is adapted to produce the Joule's heat, and will be described herein.

Further, the at least one energy inlet port 8 is electrically coupled with the wire member 7 to supply electric current along the wire member 7 in at least one of a Direct Current (DC) form to produce an electric resistance heating, or an Alternate Current (AC) form to produce an electromagnetic heating, singularly or in combination.

For example, the heat energy source for raising the core holder temperature may be obtained by either electric resistance heating and/or electromagnetic heating. In the electric resistance heating, DC current is passed through the wire member 7 coiled along an internal wall of the flexible sleeve 4, and the loss in power taking place as the current flows through the coil made from the wire member 7 is converted to heat energy, a phenomenon referred to as the Joule's heating. The electromagnetic energy may be obtained by applying AC current to the coil made from the wire member 7 surrounding the core sample, thereby generating magnetic field as the current flows through the coil made from the wire member 7, and induced loss (hysteresis loss) which produces heat. Likewise, the electromagnetic induction generates a spiral current (eddy current) as the magnetic field alternates with the AC in a spiral form. This eddy current produces Joule heating due to the electromagnetic energy heat loss (eddy-current loss).

Further, in one embodiment, the at least one circuit breaker member 9 is electrically coupled to the wire member 7 and the at least one energy inlet port 8 to control the supply of electric current across the one or more section(s) within the flexible sleeve depending upon a length of the core sample 5 for a given experiment. In one example, the maximum allowable core sample length may be 12" inches (30 cm). Furthermore, the at least one elongated thermocouple member 10 is electrically configured to monitor the temperature inside one or more section(s) of the flexible sleeve. In one embodiment, the at least one energy inlet port 8, the at least one circuit breaker member 9, and the at least one elongated thermocouple member 10 are pierced through the cylindrical pressure chamber 1 into the flexible sleeve 4 to be electrically coupled internally with the wire member 7.

The present disclosure is advantageous in overcoming the shortcomings of the conventional design by providing an improvement to existing core holder designs by incorporating multiple heat energy sources into a single core holder assembly, including electrical and electromagnetic heat energy. More so, the heat is generated inside the sleeve holding the core sample and the injected fluid, hence making it faster to attain a specific temperature condition and more efficient compared to previous designs. The generated heat can be applied singly and/or in combination of both and can be applied in a specific section along the entire length of the core holder sleeve. The present invention made use of carbon composite fiber material which can substantially withstand any pressure and temperature as well as leak-proof testing of the core holder at any condition for the pressure chamber. Likewise, the core holder sleeve is composed of flexible neoprene rubber with an internal Teflon lining to provide reasonable chemical and thermal stability, as well as non-corrosivity of the sleeve. Openings (ports) for energy inlet, fluid inlet/outlet, pressure sensors and thermocouples are provided as discussed in the claims above.

The core holder may be used in a laboratory scale core flooding experiment and assembled with different heat energy sources which includes electrical and electromagnetic heat energy sources that can be applied alone or in combination. The heat is generated and transmitted through a nichrome wire that is coiled on the internal walls of the sleeve, and the energy can be applied in specific sections along the entire length of the core holder sleeve to subject a geological core sample to a typical reservoir temperature condition. A cylindrical chamber fabricated with carbon fiber composite material is provided for hydrostatically confining the core sample to mimic a typical reservoir pressure condition whilst simultaneously allowing the injection and discharge of fluid in and from the core sample through a disk-shaped flange arranged on both ends of the core holder. Multiple openings (ports) were provided in the core holder design for energy inlet into the sleeve, temperature and pressure sensors, circuit-braking sockets and the injection of confining fluid into the annulus between the sleeve and the tubular pressure chamber, and a measure to guarantee uniform fluid migration into the pores, through the pores and out of the pores from the contact surface of the core sample.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, and to thereby enable others skilled in the art to best utilize the present disclosure and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present disclosure.

What is claimed is:

1. A multi-heat energy source core sample holder assembly for conducting experiment on a core sample in a laboratory, the multi-heat energy source core sample holder comprising:
   a core sample holder having a cylindrical pressure chamber and a pair of disk-shaped flanges positioned along opposite ends of the cylindrical pressure chamber, the pair of disk-shaped flanges defining a first disk-shaped flange and a second disk-shaped flange, the first disk-shaped flange accommodating at least one fluid injection port, and the second disk-shaped flange accommodating at least one fluid discharge port;
   a flexible sleeve arranged within and along the cylindrical pressure chamber to define more than one section to hold the core sample, and the flexible sleeve adapted to be securely sealed within the cylindrical pressure chamber to the pair of disk-shaped flanges and the core sample; and
   a multi-heat energy generation source arrangement having:
      a wire member coiled along an internal wall of the flexible sleeve,
      more than one energy inlet port electrically coupled with the wire member to supply electric current along the wire member in at least one of a Direct Current (DC) form to produce an electric resistance heating, or an Alternate Current (AC) form to produce an electromagnetic heating, singularly or in combination, and
      at least one circuit breaker member electrically coupled to the wire member and at least one energy inlet port to control the supply of electric current across more than one section within the flexible sleeve depending upon a length of the core sample for a given experiment, and
      at least one elongated thermocouple member to monitor a temperature inside of the flexible sleeve.

2. The multi-heat energy source core sample holder assembly as claimed in claim 1 further comprising an elastomeric O-ring, and wherein each of the first and second disk-shaped flange comprises a circumferential groove along which the elastomeric O-rings is disposed to form a high-pressure seal between each of the first and second disk-shaped flange and an inner surface along respective opposite ends of the cylindrical pressure chamber.

3. The multi-heat energy source core sample holder assembly as claimed in claim 1 further comprising an annular space defined between the cylindrical pressure chamber and the flexible sleeve.

4. The multi-heat energy source core sample holder assembly as claimed in claim 3 further comprising at least one fluid injection port pierced through the cylindrical pressure chamber to extend up to the annular space to inject a confining fluid in the annular space, wherein the confining fluid is one of water, oil or gas.

5. The multi-heat energy source core sample holder assembly as claimed in claim 4 further comprising a pressure control member arranged in the annular space to maintain the confining fluid in the annular space at a predetermined pressure.

6. The multi-heat energy source core sample holder assembly as claimed in claim 1, wherein the core sample holder comprises a threaded profile formed along an inner surface along each of the opposite ends to threadedly coupled with the pair of disk-shaped flanges positioned along opposite ends of the cylindrical pressure chamber.

7. The multi-heat energy source core sample holder assembly as claimed in claim 1, wherein each, the first disk-shaped flange and the second disk-shaped flange of the pair of disk-shaped flanges comprises an end plug on which respective opening of the at least one fluid injection port to inject reservoir fluids, and at least one fluid discharge port to discharge the reservoir fluids while the migration and core sample interactions are studied.

8. The multi-heat energy source core sample holder assembly as claimed in claim 7 further comprising a sand-screen assembly coupled to respective end plugs of the first disk-shaped flange and the second disk-shaped flange of the pair of disk-shaped flanges to restrict the migration of fine particles from the core sample.

9. The multi-heat energy source core sample holder assembly as claimed in claim 1, wherein the cylindrical pressure chamber is composed of one of carbon fiber composite material or its equivalent steel grade material.

10. The multi-heat energy source core sample holder assembly as claimed in claim 1, wherein the flexible sleeve is composed of a flexible neoprene rubber with an internal Teflon (polytetrafluoroethylene PTFE) lining therealong.

11. The multi-heat energy source core sample holder assembly as claimed in claim 1, wherein the wire member is a nichrome metal wire.

12. The multi-heat energy source core sample holder assembly as claimed in claim 1, wherein the more than one energy inlet port is pierced through the cylindrical pressure chamber into the flexible sleeve to be electrically coupled with the wire member.

13. The multi-heat energy source core sample holder assembly as claimed in claim 1, wherein the at least one circuit breaker member is pierced through the cylindrical pressure chamber into the flexible sleeve to be electrically coupled to the wire member and at least one energy inlet port.

14. The multi-heat energy source core sample holder assembly as claimed in claim 1, wherein the at least one elongated thermocouple member is pierced through the cylindrical pressure chamber into the flexible sleeve.

15. A multi-heat energy generation source arrangement for a multi-heat energy source core sample holder assembly to conduct experiment on a core sample, the multi-heat energy generation source arrangement comprising:
a wire member coiled along an internal wall of a flexible sleeve accommodated with a cylindrical pressure chamber of a core sample holder, the flexible sleeve defining more than one section to hold the core sample;
more than one energy inlet port electrically coupled with the wire member to supply electric current along the wire member in at least one of a Direct Current (DC) form to produce an electric resistance heating, or an Alternate Current (AC) form to produce an electromagnetic heating, singularly or in combination; and
at least one circuit breaker member electrically coupled to the wire member and at least one energy inlet port to control the supply of electric current across more than one section within the flexible sleeve depending upon a length of the core sample for a given experiment.

16. The multi-heat energy generation source arrangement as claimed in claim 15 further comprising at least one elongated thermocouple member to monitor a temperature inside one or more section(s) of the flexible sleeve.

17. The multi-heat energy generation source arrangement as claimed in claim 15, wherein the more than one energy inlet port, the at least one circuit breaker member, and the at least one elongated thermocouple member are pierced through the cylindrical pressure chamber into the flexible sleeve to be electrically coupled with the wire member.

18. The multi-heat energy generation source arrangement as claimed in claim 15, wherein the wire member is a nichrome metal wire.

* * * * *